United States Patent [19]

Patchornik

[11] Patent Number: 5,576,216
[45] Date of Patent: Nov. 19, 1996

[54] UNIVERSAL STANDARD REAGENTS, METHOD OF PREPARING SAME AND USE THEREOF

[75] Inventor: Avraham Patchornik, Nes Ziona, Israel

[73] Assignee: Zipora Patchornik, Nes-Ziona, Israel; a part interest

[21] Appl. No.: 362,519

[22] PCT Filed: Jul. 14, 1993

[86] PCT No.: PCT/US93/06980

§ 371 Date: Jan. 5, 1995

§ 102(e) Date: Jan. 5, 1995

[87] PCT Pub. No.: WO94/01771

PCT Pub. Date: Jan. 20, 1994

[30] Foreign Application Priority Data

Jul. 14, 1992 [IL] Israel ......................................... 102495

[51] Int. Cl.$^6$ ................................................ G01N 33/00
[52] U.S. Cl. ................... 436/86; 436/8; 436/34; 436/79; 436/89; 436/94; 436/111; 436/126; 436/129; 436/161; 436/164; 436/166; 436/172
[58] Field of Search ........................ 436/8, 34, 79, 86, 436/89, 90, 94, 111, 126, 129, 161, 162, 164, 166, 172, 183, 800; 534/487; 560/173, 177, 179, 180; 562/427, 437; 564/86, 368, 369, 441

[56] References Cited

U.S. PATENT DOCUMENTS

| | | |
|---|---|---|
| 2,434,564 | 1/1948 | Hester et al. . |
| 2,636,032 | 4/1953 | Weston et al. . |
| 3,978,045 | 8/1976 | Okamoto et al. . |
| 4,148,791 | 4/1979 | Altermatt . |

FOREIGN PATENT DOCUMENTS 61-3066  1/1986  Japan .

OTHER PUBLICATIONS

K. C. Ingham et al. *Biochim. Biophys. Acta* 1981 670, 181–189.
L. Lorand et al. *Anal. Biochem.* 1983, 131, 419–425.
P. J. Ryan et al. *J. Chromatog.* 1984, 312, 461–466.
I. Yanagisawa et al. *J. Chromatog.* 1985, 345, 229–240.
H. Lingeman et al. *Chem. Abstr:* 1987, 106, 168383h.
G. H. Keller et al. *Anal. Biochem.* 1988, 170, 441–450.
A. Junker-Buchheit et al. *Fresenius Z. Anal. Chem.* 1988, 331, 387–393.
Y. M. Lee et al. *J. Chromatog.* 1990, 515, 467–473.
E. Grunwald et al. *J. Am. Chem. Soc.* 1964, 86 2970–2977.
Chemical Abstracts, vol. 59, No. 43, Issued 19 Aug. 1963, Abramzon et al., "Kinetics of reactions in heterogeneous systems. IV. Rate of mass transfer in complex chemical reactions in heterogeneous liquid–Liquid systems." 3349–3350, *Zh. Prikl. Khim.* 36, (1963). 608–13.

Chemical Abstracts, vol. 63, No. 4, Issued 16 Aug. 1965, Sieler et al. "Determination of amine at $10^{-10}$ molar. Separation of dimethylaminonaphthalene–5–sulfonamides by thin–layer chromatography." *Experientia* 21 (1965), 203–4.
Chemical Abstracts, vol. 76, No. 7, Issued 14 Feb. 1972, Nilsson et al., "Fibrin–stabilizing factor inhibitors. III. Sulfonamides related to monodansylcadaverine." abstract No. 33988a, *Acta Pharm. Suecica* 8 (9171), 497–504.
Chemical Abstracts, vol. 94, No. 15, Issued 13 Apr. 1981, Wangyi et al., "A new flourescent hydrazide for sequencing ribonucleic acids." abstract No. 94:11729h, *Sci. Sin. (Engl. Ed.)* 23, (1980), 1296–308.
Chemical Abstracts, vol. 101, No. 8, Issued 20 Aug. 1984, Al-Hajjiji, "2,4,6–Trinitrophenyl–amino acid derivatives as spectrophotometic reagents for sulfer dioxide." abstract No. 101:65162c, *Anal. Lett.* 17(A4), (1984), 297–308.
Chemical Abstracts, vol. 112, No. 8, Issued 19 Feb. 1990, Kallmayer et al., "Testing for purity of piperazine—investigations employing tests from the European and 9th German pharmacopeias and tests involving derivatization with dansyl chloride. Part 2. Analytical reactions of ethylenediamines." abstract No. 112:62749r, *PZ Wiss*, 2, (1989), 18–24.
Journal of the Chemical Society, Issue 1943, Quin et al., "Attempts to find New Antimalarials. Part XVIII." pp. 556–556.
Hoppe–Seyler's Zetschrift fur Physiologische Chemie., vol. 296, Issued 1954, Jatzkewitz et al., "Darstellung und papierchromatographische trennung einiger dinitrophenyl–aminoalkohole", pp. 188–192.
Journal of the Chemical Society, Issued Sep. 1956, Newlands et al., "Janovsky reaction.", p. 3696.
The Journal of Biochemistry, vol. 50, No. 2, Issued 1961, Oikawa et al., "Some properties of DNP–amines," pp. 157–158.
Journal of Chromatography, vol. 20, Issued 1961, Oikawa et al., "Some properties of DNP–amines", pp. 157–158.
The Biochemical Journal, vol. 88, No. 1, Issued 1963, Matheson, "An Improved Method of Separating Amino Acids as N–2,4–Dinitrophenyl Derivatives", pp. 146–151.

(List continued on next page.)

*Primary Examiner*—Arlen Soderquist
*Attorney, Agent, or Firm*—Browdy and Neimark

[57] ABSTRACT

A universal standard chemical reagent for quantitative visual and spectrometric analysis of compounds having reactive functional groups, including mixtures and homologs of said compounds, said reagent comprising a compound of the general formula Q-B-f, wherein: Q stands for an organic moiety which can be measured quantitatively, visually by color, spectroscopically, or fluorometrically; B represents a non-reactive organic bridging unit linking the moiety Q to a reactive functional group f, said bridging unit being of sufficient length or size to prevent any possible interaction of Q that might alter its spectroscopic properties even upon derivatization; and f is a reactive group which can react with a compound to form covalently bonded derivatives.

9 Claims, No Drawings

OTHER PUBLICATIONS

Journal of Chromatography, vol. 24, Issued 1966, Silaev et al., "Quantitative Determination of α and π–2,4–Dinitrophenyl–Isomers of, α and π–diaminobutryic Acid with an Automatic Acid Analyzer as a Method of Studying . . . ". pp. 61–67.

Archives of Biochemistry and Biophysics, vol. 155, Issued 1973, Yang et al., "Covalent Attachment of Fluorescent Groups to the 5'-End of Transfer RNA", pp. 70–81.

Journal of Pharmaceutical Sciences, vol. 66, No. 8, Issued Aug. 1977, Abdel–Monem et al., "Polymine Metabolism I: Synthesis of Dansyl Derivatiaves of N–(Monoaminoankyl)– and N–(Polyaminoalkyl)acetamides and Elucidation in Urine of a Cancer Patient", pp. 1089–1094.

Biochemistry, vol. 20, Issued 1981, Guyon–Gruaz et al., "Conformational Studies of Dansylated Enkephalins by Fluorescence Transfer Measurements, Proton Nuclear Magnetic Resonance Spectroscopy, and Theoretical Calculations", pp. 6677–6683.

Nucleic Acids Research, vol. 14, No. 15, Issued 1986, Agrawal et al., "Efficient methods for attaching non–radioactive labels to the 5'ends of synthetic oligodeoxyribonucleotides", pp. 6227–6245.

Journal Chromatography, vol. 44, Issued 1988, Szokan et al., "Application of Marfey's Reagent in Racemization Studies of Amino Acids and Peptides", pp. 115–122.

Analytical Chemistry, vol. 61, Issued 1989, Chou et al., "Chiral Plymeric Reagents for Off–Line and On–Line Derivatization s of Enantiomers in High–Performance Liquid Chromatography withUltra violet and Fluorescence Detection: An Enantiomer Recognition Approach", pp. 1548–1558.

Nucleic Acids Research, Col. 18, No. 11, Issued 1990, Singh et al., "Oligonucleotides, part 5+:synthesis and fluorescence studies of DNA oligomers d(AT)5 containing adenines covalently linked at C8 with dansyl fluorophore", pp. 3339–3345.

Biochimica et Biophysica Acta, vol. 1085, Issued 1991, Crawford et al., "Physical and biological prperties of flluorescent dansylated bile salt derivatives: the role of steroid ring hydroxulation", pp. 223–234.

Analytical Chemistry, vol. 59, issued 1987, Lin et al., "Synthesis of Dabsylhydrazine and Its Use in the Chromatographic Determination of Monosaccarides by Thin–Layer and High–Performance Liquid Chromatography", pp. 1320–1326.

Chemical Abstracts, vol. 93, No. 7, Issued 18 Aug. 1980, Klimek et al., "Determination of DNA–amino acids depending o the maximum and minimum of absorption in the ultraviolet", abstract No. 94:72234s, *Ann. Univ. Mariae Curie–Sklodowska, Sect. D,* 33, (1978), 141–8.

Biochemistry Journal, vol. 124, Issued 1971, Kaplan et al. "Competitive Labelling, a Method for Determining the Reactivity of Individual Groups in Proteins.", pp. 289–299.

Journal of Chromatography, vol. 282, Issued 1983, Einarsson et al., "Determination of Amino Acids with 9–Fluorenyulmethyl Chloroformate and Reversed–Phase High-Performance Liquid Chromatography", pp. 609–618.

UNIVERSAL STANDARD REAGENTS, METHOD OF PREPARING SAME AND USE THEREOF

The present invention relates to a new class of chemical reagents for quantitatively measuring compounds containing reactive functional groups. The invention further relates to methods of preparing such reagents and using them. Specifically, the invention relates to a new class of chemical reagents which can be used as universal standards for quantitatively measuring any compound which can form a derivative with the reagents when the compound is present in mixtures and together with homologs. More specifically, the reagents of this invention are organic chemicals which have specific moieties that can be measured quantitatively, colorometrically, fluoroscopically, or by other spectral means such as UV, IR, NMR and ESR. Some of these reagents are new chemical compounds.

It is thus an object of this invention to provide a new class of analytical reagents which can serve as universal standards for visual spectroscopic analysis of different compounds, without requiring comparison with a standard for each compound measured.

Another object of the present invention is to provide analytical methods for measuring compounds quantitatively, with reagents whose molar $\epsilon$ and that of their derivatives is substantially constant.

Yet another object of the invention is to provide a method of quantitatively measuring homologous compounds with a single standard reagent without requiring external standards.

A further object of the invention is to provide some new chemical compounds suitable for use as universal standard colorimetric or spectrometric analytical reagents.

Until now, the common methods for quantitatively measuring chemical compounds having functional groups were based on the reaction of these compounds via their functional groups with a reagent, usually a chromophoric or fluorescent reagent, and measuring the derivative spectrometrically by comparing the absorption of this derivative with that of a known external standard of such a derivative compound. For example, the determination of amino acids with fluoro-2,4-dinitrobenzene (FDNB) as described by Sanger, *Biochem. J.*, Vol. 45, p. 563 (1984), is carried out by converting the amino acids into their dinitrophenyl derivatives. The actual quantification of each amino acid is arrived at by comparing the UV absorption of the corresponding dinitrophenyl derivative with that of standard amino acid dinitrophenyl products, e.g., DNP-Gly, DNP-Ala, etc. The external standard, however, is different for each amino acid measured. Similarly, amino acids can be analysed quantitatively fluorometrically by reacting them with a fluorescent reagent such as Dansyl chloride, Dabsyl chloride or O-pthalaldehyde to form the fluorescent derivative. The actual quantification again requires a specific external standard for each amino acid.

The present invention provides a new universal standard chemical reagent for quantitative visual and spectrometric analysis of compounds having reactive functional groups, including mixtures and homologs of said compounds, said reagent comprising a compound of the general formula I:

Q-B-f     (I)

wherein Q stands for an organic moiety which can be measured quantitatively, visually by color, spectroscopically or fluorometrically; B represents a non-reactive organic bridging unit linking the moiety Q to a reactive functional group f, said bridging unit being of sufficient length or size to prevent any possible interaction of Q that might alter its spectroscopic properties even upon derivatization; and f is a reactive group which can react with a compound to form covalently bonded derivatives.

As stated, said bridging unit B is of sufficient length and/or size to prevent any possible special interaction of Q that might alter its spectroscopic properties even upon derivatization. This is particularly relevant for fluoroscopic analysis where interference is possible even from a distance.

Furthermore, as indicated, f is any reactive group which can react with a compound to form covalently bonded derivatives having the formula Q-B-f-A. Such a reaction can be represented as follows:

n(Q-B-f)+A→Q-B-f-A+(n−1)Q-B-f wherein A represents any analysable compound containing a reactive functional group that will form a covalent bond with the reactive group f.

The invention also provides a method for the quantitative determination of an organic compound designated herein by A, said compound A having a reactive functional group, said method comprising:

reacting a sample containing said compound A with a reagent comprising a compound of the general formula I:

Q-B-f     (I)

wherein:

Q stands for an organic moiety which can be measured quantitatively, visually by color, spectroscopically, or fluorometrically;

B represents a non-reactive organic bridging unit linking the moiety Q to a reactive functional group f, said bridging unit being of sufficient length or size to prevent any possible interaction of Q that might alter its spectroscopic properties even upon derivatization; and f is a reactive group which can react with a compound to form covalently bonded derivatives, according to the reaction:

n(Q-B-f)+A→Q-B-f-A+(n−1)Q-B-f wherein

Q, B, and f are as defined as above and n equals 1 or more;

separating any excess reagent (n−1)Q-B-f; and measuring the absorption of the reaction product Q-B-f-A wherein the molar absorptivity of $\epsilon$ of said reaction product Q-B-f-A and said reagent Q-B-f are substantially constant and wherein the molar concentration of the reaction product Q-B-f-A is equal to the measured absorption divided by $\epsilon$, thus eliminating the requirement for comparing the measured result with an external standard.

Preferably, in said method, said molar absorption is measured spectroscopically or visually.

Said method is especially applicable for the determination of amino acids, and the invention also provides a method for determining mixtures of amino acids, comprising reacting said mixture of amino acids with a reagent according to the present invention; separating the amino acid reaction products; and measuring said products spectroscopically with said reagent serving as a universal standard for all the amino acid reaction products.

In another aspect of the present invention, there is also provided a method for studying reaction rates of functional groups present in different types of compounds, comprising:

reacting a known mixture of compounds having the same functional group with less than stoichiometric amounts of a reagent comprising a compound of the general formula I:

Q-B-f                  (I)

wherein:

Q stands for an organic moiety which can be measured quantitatively, visually by color, spectroscopically, or fluorometrically;

B represents a non-reactive organic bridging unit linking the moiety Q to a reactive functional group f, said bridging unit being of sufficient length or size to prevent any possible interaction of Q that might alter its spectroscopic properties even upon derivatization; and f is reactive group which can react with a compound to form covalently bonded derivatives;

separating the derivative reaction products; and measuring the absorption of each derivative product using the reagent as a universal standard, the reaction rates of the functional groups present in each of the different compounds being proportional to the molar concentration of each of the derivative products.

In this method, said reaction products are preferably chromotographically separated.

Generally, the compounds to be analyzed and measured are reacted with an excess reagent Q-B-f and the product is isolated from excess reagent by known methods of separation such as chromatography, or by adding excess of another reactive compound A' similar to A in its chemistry, but carrying a functional group that can help in separating the excess reagent Q-B-f from the reaction mixture. Such compounds A' may be polymers with functional groups similar to those of A which upon reaction with excess reagent form separable solids. A' could also contain functional groups such as -SO₃H or -N- which would make the reaction product with Q-B-f water soluble or separable. The product is then measured visually by color or spectroscopically. The molar concentration of the reagent and derivative will have the same ε irrespective of which compound A is being determined in the reaction is quantative.

Some representative moieties for Q are shown in Table 1.

TABLE 1

| Name | Structural formula |
| --- | --- |
| 2.4 dinitro-phenylamino- | $O_2N-\text{C}_6H_3(NO_2)-NH-$ |
| 2.4 dinitro-phenyl-N< | $O_2N-\text{C}_6H_3(NO_2)-N<$ |
| dansyl amido- | $SO_2NH-$ naphthalene-N(CH₃)₂ |

TABLE 1-continued

| Name | Structural formula |
| --- | --- |
| dansyl-N< | $SO_2-N<$ naphthalene-N(CH₃)₂ |
| dansyl- | $SO_2-$ naphthalene-N(CH₃)₂ |
| dansyloxy- | $SO_2O-$ naphthalene-N(CH₃)₂ |
| dabsylamido- | $(CH_3)_2N-\text{C}_6H_4-N=N-\text{C}_6H_4-SO_2NH-$ |
| dabsyl-N< | $(CH_3)_2N-\text{C}_6H_4-N=N-\text{C}_6H_4-SO_2N<$ |
| dabsyl- | $(CH_3)_2N-\text{C}_6H_4-N=N-\text{C}_6H_4-SO_2-$ |
| dabsyloxy- | $(CH_3)_2N-\text{C}_6H_4-N=N-\text{C}_6H_4-SO_2O-$ |
| fluoren-9-yl-methyloxy-carbonyl- (FMOC) | fluorenyl-$CH_2-OCO-$ |
| fluoren-9-yl-methyloxy-carbamido- | fluorenyl-$CH_2-OCONH-$ |
| fluoren-9-yl-methyloxy-carbonato- | fluorenyl-$CH_2-OCOO-$ |

Some representative bridging units B are:

$(C_nH_{2n})$- where n=2 to 18;

$(C_mH_{2m}Z)_p$ where m=2 to 3, Z=NH, O, S and p=1 to 18;

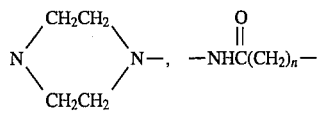

where n and m are as defined above.

Some representative reactive functional groups f that can be reacted with compounds A to form spectroscopically measurable derivatives not requiring any external standard are listed in Table 2.

$A_1$ and $A_2$ by reacting an excess of each of $A_1$ and $A_2$ with the same analytical reagent Q-B-f. The ratio of the amounts of their respective products Q-B-f-$A_1$ and Q-B-f-$A_2$ is a measure for their relative reactivities. For example, when 10 equivalents of acetic anhydride ($A_1$=$CH_3CO$) and 10 equivalents of benzoic anhydride ($A_2$=$C_6H_5CO$) are reacted with 1 equivalent of DNP-NH($CH_2$)$_2$ $NH_2$, the ratio in which their products, DNP-NH($CH_2$)$_2$NHCOCH$_3$ and DNP-NH($CH_2$)$_2$ NHCOC$_6$H$_5$, respectively, are found in the resulting reaction mixture is a measure for the reactivity of acetic anhydride and benzoic anhydride as acylating agents.

TABLE 2

| f-group | Suitable for measuring the Following A Groups |
| --- | --- |
| 1) —$NH_2$ | acylating, sulphonating or phosphorylating reagents, reactive esters, aldehydes, mixed anhydrides, carbon dioxide, alkylating epoxides, acrylates, β-lactams |
| 2) —NH-$R_1$ | as for 1), except for aldehydes |
| 3) —$NHR_1R_2$ | alkylating reagents ($CH_3X$, X = Halogen) |
| 4) —$N^{\oplus}R_1R_2R_3$ | ionic reagents in aqueous solution (ion exchange reaction) |
| 5) —COOH | $CH_2N_2$, $ArCHN_2$, ROH or RSH (DCC coupling method) |
| 6) —CO—OL<br>—OL = leaving group such as OBT, O—SUC, nitrophenol etc. | Nucleophiles, such as —$NH_2$, NHR, —$NHR_1R_2$, ROH, RSH, $CN^{\ominus}$, $N_3^{\ominus}$, etc. |
| 7) —CO NH $NH_2$ | aldehydes, saccharides |
| 8) —NH $COCH_2X$<br>(X = Halogen) | RSH |
| 9) —$NHCOCH_2CH_2CH_2SH$ | alkylating reagents such as alkyl halogens, activated double bond (Michael addition) as in acrylates |
| 10) —$CH_2$—CH=$CH_2$ | halogens and H-hal |
| 11) —$CH_2$-hydroxy quinoline EDTA, hydroxamates | $Zn^{2+}$, $Cu^{++}$, Au, $Ca^{++}$ |
| 12) —CHO | $SO_2/H_2O$, ROH, RSH, $CN^{\ominus}$, proteins with or without help of $NaBCNH_3$ |
| 13) —$SO_3H$ | amine salts, basic inorganic salts, i.e. Na, K, Ca |
| 14) —$SO_2NH$ $NH_2$ | R CHO, $Br_2$, $Cl_2$, $I_2$ (RCO)$_2$O and acylating reagents; aldehydes |
| 15) —$CH_2$ | a model for aromatic Friedel Craft reactions |
| 16) COOCH$_3$ | kinetics of ester hydrolysis, hydrazinolysis, aminonolysis |
| 17) —$CH_2S_3Hal$ | selective for indoles and derivatives |
| 18) OH | as models for sugars in the formation of glycosidic bonds |

For example, in the analytical reagent DNPNH($CH_2$)$_2NH_2$, DNP=2,4-dinitrophenyl, Q=2,4-dinitrophenylamine (DNP-NH-), B=—($CH_2$)$_2$— and f=-$NH_2$. We measured various acyl compounds with this reagent. By mixing excess DNPNH($CH_2$)$_2NH_2$ with an unknown acylating (RCO$^+$) compound, DNP-NH($CH_2$)$_2$NHCOR is formed. After removal of excess reagent, the new derivative compound can be measured spectrometrically, its measured value being proportional to the amount of RCO$^+$. The acylating compound can encompass a wide variety of acylating groups such as RCO$^+$, $CH_3$CO—, $C_6H_5$CO—, t-BuOCO—, $ArSO_2$—, etc.

Similarly, the analytical reagent DNPNH($CH_2$)$_2$COOSu, (Su=succinimide), where Q=DNPNH—, B=—($CH_2$)$_2$— and f=COOSu, was successfully reacted with a wide variety of compounds carrying a primary or secondary amine function such as ($C_2H_5$)$_2$NH, $C_6H_5NH_2$, $H_2NNH_2$, $C_6H_5CH_2NH_2$, HO-($CH_2$)$_3$NH2, HS($CH_2$)$_2NH_2$, to give derivatives that can be determined spectroscopically without external standards. Using excess succinimide active esters as reagent gives quantitative conversion of the amines to amides.

In addition to using the reagents of this invention for the quantitative determination of compounds, it is possible to determine the relative reactivities of two given compounds The reagents of this invention are also useful for measuring reactive gases. Thus, carbon dioxide can be measured in a very convenient way by reacting it with a toluene solution of DNP-NH($CH_2$)$_2NH_2$, as follows:

DNP-NH(CH$_2$)$_2$NH$_2$ + CO$_2$ 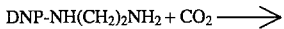

(yellow, insoluble in water)

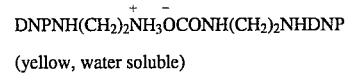

(yellow, water soluble)

The latter compound is a colored salt and can be extracted with water and measured spectrometrically. Remnants of the original reagent will dissolve in toluene.

With this class of reagents it is possible to follow reactions involving colored chromophores by visual examination with very small quantities (nanomoles).

In accordance with this invention, not only soluble material or gases can be analysed with the novel universal standard reagents, but it is also possible to determine quantitatively heterogeneous matrices such as found in polymers and polymeric reagents, which can be covalently bound to the reagents.

Thus, e.g., when an insoluble, but swellable polymer P has a reactive group A attached to it, the reactive polymer can be represented by the formula ⓅI-α-A. α is the linking group between the insoluble polymer matrix Ⓟ and the group A and is covalently bound to Ⓟ and stable to any cleavage during the chemical manipulation. This polymer, when reacted with excess of a reagent Q-B-f, forms reaction products which are (1) insoluble polymer -Ⓟ-α itself; and (2) Q-B-f-A, where Q, B, f and A are as defined above. After removing the excess reagent Q-B-f, and the polymer -Ⓟ-α- from the reaction mixture, the amount of A originally bound to a given weight of polymer Ⓟ-α-A can be calculated by measuring spectrometrically the amount of Q-B-f-A formed. The value found for Q-B-f-A is then proportional to the original amount of A attached to the polymer Ⓟ-α-A.

More specifically, the amount of reactive $RCO^{30}$ groups bound to a polymer can be determined as shown by the equation:

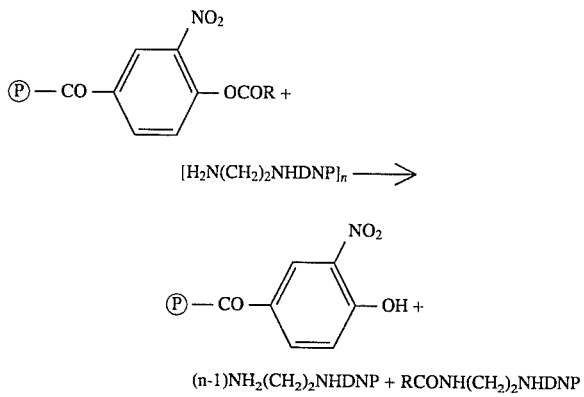

wherein n is a whole integer.

Alternatively, the reactive polymer may be of the kind represented by Ⓟ -A, where A is covalently bound to the polymeric matrix. Here, too, excess reagent Q-B-f is used to react with the polymer to give a high yield of reaction to form Ⓟ -A-f-B-Q and the excess reagent is washed out. In this case, additional chemical cleavage is necessary to release the Q group to be measured. Special, easily hydrolyzable or cleavable groups are used. To mention a few: ester (—COO—), amide (—CONH—), carbamide (—OCONH—) and S—S bonds are quite often used.

In cases where the reactive polymer mentioned above, Ⓟ-α-A, comprises an active ester group, then the α ($\alpha = CN^{31}$, $n_3^-$, benzhydroxythiazole [BTOH], imidazole, etc.), forms an unstable compound RCOα in solution. To measure the quantity of RCOα an excess of $DNPNH(CH_2)_2NH_2$ is added to the filtrate of the reaction mixture, and a stable compound $RCOHN(CH_2)_2NHDNP$ is formed and measured easily as described. This allows the measurement of polymeric-bound active reagent and soluble RCOα.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Determination of Functional Groups on Solid Support

EXAMPLE 1

Equal aliquots ($5 \times 10^{-4}$M) of a solution of 2,4-dinitrophenyl amino ethylenediamine $DNPNH(CH_2)_2NH_2$) in $CH_2Cl_2$ were reacted with equal volumes $25 \times 10^{-4}$M of a solution of the following compounds in $CH_2Cl_2$:

1. acetyl chloride
2. acetic anhydride
3. benzoyl chloride
4. tosyl chloride
5. trimethylsilyl chloride
6. oxalyl chloride
7. thionyl chloride To each reaction mixture a five-fold excess of triethyl amine, with respect to the chloride, was added to prevent the formation of the HCl salts of the intended products (except for reaction mixture 2, where it cannot be formed). The formation of the expected products was confirmed by TLC analysis of a second series of equal reaction mixtures.

It was shown that in all cases 1–7 the UV-absorption measured at ≈3480A was the same as for the original reagent. This shows that the different acyl groups attached to $DNPNH(CH_2)_2NH_2$ have no influence on the absorption spectrum of the chromophore, because of the ethylene bridging unit. It also shows that $DNPNH(CH_2)_2NH_2$ is a sensitive reagent for quantifying various acylating reagents when used in excess and the excess is removed by flash chromatography after completion of the reaction. HCl salts have a slightly different e value because of an altered chromophore as compared to that in 2,4 dinitrophenyl amino ethylene diamine.

For separating the excess $DNPNH(CH_2)_2NH_2$ reagent from the acylated product, a quite simple and effective procedure was found, using a separation column as follows:

A column having a diameter of about 4 mm and length of 2–4 cm was filled with a mixture comprising 90% silica and 10% polymeric sulfuric acid ion exchange resin. The acylated reaction mixture was poured onto the column. The acylated $DNPNH(CH_2)_2NH_2$ was eluted with 0.2 to 2 ml of solvent such as methylene chloride or ethyl acetate, optionally containing up to 30% methyl, ethyl or isopropyl alcohol. The excess $DNPNH(CH_2)_2NH_2$ remained on the column. This separation method is good for detecting quantities as low as 1 mm.

EXAMPLE 2

Equal aliquots ($5.3 \times 10^{-4}$M) of a solution of $DNP-NH(CH_2)_2COOSu$ in $DMSO/CH_2Cl_2$ were reacted with equal aliquots ($25 \times 10^{-4}$M) of solutions of the following amines in $DMSO/CH_2Cl_2$:

1. $(C_2H_5)_2NH$
2. $C_6H_5CH_2NH_2$
3. $H_2NNH_2$
4. $C_6H_5NH_2$
5. $HS—CH_2—CH_2NH_2HCl$
6. $HO_3S—CH_2—CH_2—NH_2—HCl$

The DNP-NH(CH$_2$)$_2$ COOSu was added in approximately two-fold excess. In reaction mixtures 5 and 6, excess triethyalmine was added. The reaction mixtures were heated (60° C.) for one hour. TLC tests (on a second equal set of reaction mixtures) showed the formation of new amide products. When the reaction mixtures were measured at ≈3480A, the UV-absorption of the products formed was similar to that of the original Q-B-f reagent. This shows that the ethylene bridging unit prevents any influence by the different amides on the DNPNH-chromophore group. Moreover, the experiment shows that DNP-NH(CH$_2$)$_2$COOSu can be used successfully as an analytical reagent for quantifying various amines, when applied in excess and the excess is removed after the completion of the reaction.

EXAMPLE 3

Equal aliquots (4×10$^{-3}$M) of a solution of dansyl ethylenediamine in CH$_2$Cl$_2$ were reacted with equal aliquots (7×10$^{-3}$M) of a solution of the following compounds in CH$_2$Cl$_2$:

1. acetic anhydride
2. benzoyl chloride
3. tosyl chloride

Compounds 2 and 3 were added in approximately five-fold excess. One equivalent triethyl amine with respect to tosyl chloride was added as well.

The formation of the expected dansyl ethylene diamine derivatives was confirmed by a TLC check of a second set of similar reaction mixtures. When the reaction mixtures were diluted to an arbitraily chosen, but exactly known, volume, and measured fluorimetrically at ≈3400A, it was found that the fluorescence of the reaction mixtures was equal to that of an equimolar dansyl ethylene diamine solution. This implies that acyl groups connected to dansyl ethylene diamine via the ethylene bridging unit do not influence the fluorescent properties of the dansyl group itself. Moreover, it shows that dansyl ethylene diamine, like DNPNH(CH$_2$)$_2$NH$_2$, can serve as an analytical reagent for quantifying various acylating compounds, when reacted in excess and the excess is removed (by flash chromatography) after completion of the reaction.

Synthesis of Reagents

EXAMPLE 4

DNP-NH(CH$_2$)$_2$NH$_2$ 90.0 g of chloro-2,4-dinitrobenzene (0.44M) was added portionwise to a cooled (0° C. stirred) solution of 179 g ethylenediamine (200 ml, 2.98M) in 400 ml methanol. The solid reactant gradually dissolved in the reaction mixture. After completion of the addition, the stirring continued for another 4 hours at 0° C.

Workup

A precipitate formed and was identified as DNP-NH-CH$_2$-CH$_2$-NH-DNP side product. It was filtered off, washed repeatedly with water and dried. Yield: 2.0 g. To the filtrate was added ice water, and the resulting precipitate was filtered and repeatedly washed with cold water. The crude product was dried. Yield: 52.0 g (52%). A further purification was made by dissolving 10 g of the crude product in 400 ml boiling 1.0 NHCl. The solution was cooled and more cold water was added. It was then extracted with ethyl acetate until TLC showed that the last extraction was clean. The aqueous fraction was made alkaline with concentrated ammonia, cooled to 0° C. and the resulting precipitate filtered off. It was washed with water several times and dried. This treatment afforded 6.5 g very pure, yellow needles.

EXAMPLE 5

DNP-NH(CH$_2$)$_2$NHCOONH(CH$_2$)$_2$NHDNP

Part of the crude DNPNH(CH$_2$)$_2$NH$_2$ prepared was dissolved in methanol and a current of carbon dioxide was led through the clear solution. A yellow, spongy precipitate formed. After 20 minutes the influx of carbon dioxide was stopped, and the precipitate filtered off, washed with cold methanol and dried.

EXAMPLE 6

DNP-NH(CH$_2$)$_6$NH$_2$ 10 g fluorodinitrobenzene (FDNB, 53.5 mM) was added portionwise to a stirred solution of 17.4 g hexamethylenediamine (150 mM) in 500 ml chloroform. The FDNB reacted quickly, and yellow precipitate was immediately formed.

Workup

After stirring for 4 hours, the precipitate formed was filtered off and the resulting filtrate was washed with 1.5 l of diethyl ether. Yield: 10.1 g (66%) tlc on silica gel in CH$_2$Cl$_2$. Rf=0.77.

EXAMPLE 7

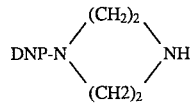

23.0 g piperazine (267 mM) and 10.0 g chlorodinitrobenzene (CDNB) (49.4 mM) were mixed (with stirring) in 150 ml of methanol at room temperature. The reactants went into solution within 10 minutes, but then a new product started to precipitate. The reaction mixture was stirred for a total of 4 hours.

Workup

The precipitate was filtered off, the filtrate evaporated to half its original volume. About 240 ml CH$_2$Cl$_2$ was added, whereupon the organic layer was washed 8 times with water. The presence of piperazine in the washings was checked with ninhydrine. Then the organic layer was extracted 6 times with HCl 4N solution; it became almost colorless. The aqueous layer in turn was made alkaline with a 25% NH$_4$OH solution and the product was washed back with CH$_2$Cl$_2$. The CH$_2$Cl$_2$ layer was dried over MgSO$_4$, filtered and evaporated till dry. The resulting orange syrup crystallized totally in about 3 weeks. Yield: 24.2 g.

EXAMPLE 8

DNPNH(CH$_2$)$_3$OH 10.1 g chlorodinitrobenzene (CDNB, 50 mM) was added at once to a cooled stirred (0° C.) solution of 11.3 g 3-aminopropanol (1.4 ml, 150 mM) in 50 ml of methanol. The CDNB went very slowly into solution; there was still some left after 1 hour. After 2 hours, the reaction mixture was brought to a boil and kept at a reflux for a few minutes. After cooling off, a yellow precipitate formed, which was filtered off, washed with a little cold methanol and sucked dry. This afforded 11.5 g of crude material (95%). Further purification could be obtained by recrystallization from hot methanol.

EXAMPLE 9

DNP-NH(CH$_2$)$_2$COOH

This synthesis was conducted in three steps:

a) HCl·H$_2$N(CH$_2$)$_2$COOCH$_3$:

17.8 g β-alanine (H$_2$N(CH$_2$)$_2$COOH, 200 mM) was partly dissolved in 200 ml dry methanol and cooled to −20° C. 20 ml SOCl$_2$ (275 mM) was added in 40 minutes, during which the cooling remained in effect. The acid went slowly into solution. Shortly after completion of the addition, the cooling was removed, allowing the reaction mixture to reach room temperature. It was stirred for 16 additional hours to remove SO$_2$.

Workup

The solution was evaporated to dryness, affording white hygroscopic crystals. They were dried in vacuo. Yield: 26.8 g white crystals (96%), mp: 99°–101° C.

b) DNP-NH(CH$_2$)$_2$ COOCH$_3$

A solution of 20.26 g CDNB (100 mM) in 50 ml THF was added dropwise to a mixture of 13.96 g HCl H$_2$N(CH$_2$)$_2$COOCH$_3$ (100 mM) and 28.0 ml triethylamine (200 mM) in 300 ml THF at room temperature. The addition lasted 2 hours and 15 minutes, while stirring vigorously. Thereafter, the stirring continued for 40 hours.

Workup

The reaction mixture was filtered off, and the resulting filtrate evaporated to dryness. The yield was 23.9 g (89%), it was an orange yellow amorphous powder.

c) DNPNH(CH$_2$)$_2$COOH 15.0 g (55.7 mM) of DNPNH(CH$_2$)$_2$COOCH$_3$ was dissolved (with periodical warming to about 40° C. of the reaction mixture) in 200 ml of a 0.5N NaOH solution (1.8 eq NaOH). The starting material dissolved slowly; the mixture was stirred for a total of 24 hours.

Workup

The solution was filtered after warming again to 50° C. The pH was brought to about 2 with concentrated hydrochloric acid. The flaky precipitate formed was filtered off and washed with ice water, and dried in vacuo. Yield: 11.13 g of a yellow, amorphous powder

EXAMPLE 10

DNPNH(CH$_2$)$_2$COONSuc 9.29 g dicyclohexyl carbodiimide (DCC, 45 mM; 1.5 eq) was added at once to a cooled (0° C.) solution of 7.65 g DNPNH(CH$_2$)$_2$COOH (30 mM) and 3.45 g N-hydroxy succinimide (3 mM) in 150 ml dry THF. The cooling remained in effect for about 2 hours, then the reaction mixture was allowed to slowly reach room temperature. Stirring continued for 72 hours.

Workup

The precipitate formed was filtered off and the filtrate evaporated to dryness. The resulting residue was recrystallized from hot iso-propanol. This afforded 6.32 g orange-brown crystals (57%).

EXAMPLE 11

DNP-NH(CH$_2$)$_2$CONHNH$_2$

A solution of 6.4 ml hydrazine (200 mM) in 35 ml iso-propanol was dropped during 10 minutes into a solution of 10.76 g DNPNH(CH$_2$)$_2$COOCH$_3$ (40 mM) in 135 ml dry THF at room temperature. After completion of the addition, the mixture was brought to a boil and refluxed for 3 hours.

Workup

The reaction mixture was filtered off over a paper filter and the filtrate left for crystallization overnight (first fraction). The concentrated mother liquor afforded a second fraction. Yield: 6.75 g (63%), fine orange-brown needles.

EXAMPLE 12

DNPNH(CH$_2$)$_2$NHCOCH$_3$

A solution of 0.785 g of acetylchloride (0.71 ml, 10 mM) in 25 mg dry THF was dropped slowly into a stirred, cooled (0° C.) solution of 2.26 g DNPNH(CH$_2$)$_2$NH$_2$ (10 mM) and 1.6 ml triethyl amine (12 mM) in 50 ml dry THF. After completion of the addition, the cooling remained in effect for 30 minutes, and it was then removed to allow the reaction mixture to reach room temperature.

Workup

The reaction mixture (rm) was evaporated to dryness. The residue was washed with small volumes of cold water over a glass filter. The resulting filter cake was dried in vacuo. Yield: 1.9 g.

EXAMPLE 13

DNPNH(CH$_2$)$_2$NHCOC$_6$H$_5$

A solution of 1.40 g benzoylchloride (1.16 ml, 10 mM) in 25 ml dry THF was added dropwise to a stirred, cooled 10° C.) solution of 2.26 g DNPNH(CH$_2$)$_2$NH$_2$ (10 mM) and 1.67 ml triethyl amine (12 mM) in 50 ml dry THF. After the end of the addition, the cooling remained in effect for 1 hour and it was then taken away to allow the reaction mixture to slowly reach room temperature.

Workup

The workup was done as in Examples 9 and 11. Yield: 2.2 g.

EXAMPLE 14

DNPNH(CH$_2$)$_2$NHSO$_2$C$_6$H$_4$CH$_3$

A solution of 1.92 g toluenesulphonyl chloride (tosyl chloride, 10 mM) in 30 ml dry THF was added dropwise to a stirred, cooled (0° C.) solution of 2.26 g DNPNH(CH$_2$)$_2$NH$_2$ (10 mM) and 1.67 ml triethyl amine (12 mM) in 50 ml dry THF. Cooling was maintained for 2 hours, then it was removed. Stirring at room temperature continued for 20 hours.

Workup

The workup was done as in Examples 9 and 10. Yield: 2.5 g.

EXAMPLE 15

DNPNH(CH$_2$)$_2$C$_6$H$_5$ 2.03 g chloro-2,4-dinitrobenzene was added portionwise to a stirred, cooled (0° C.) solution of 6.1 g phenethylamine (6.3 ml, 50 mM) in 100 ml methanol. After all CNDB had reacted away (4 hours) the ice bath was removed.

Workup

To the reaction was added ice water, and the pH made acidic with concentrated hydrochloric acid. The precipitate formed was filtered off and washed several times with cold water over a glass filter. The filter cake was dried in vacuo. Yield: 2.5 g.

EXAMPLE 16

DNPNHCH$_2$-CH=CH$_2$ 3.05 g chloro-2,4-dinitrobenzene (15 mM) was added portionwise to a cold, stirred solution of 8.57 g allylamine (11.25 ml, 150 mM) in 100 ml of methanol. Stirring continued at 0° C. for 4 hours and then for 18 additional hours at room temperature.

Workup

The addition of ice water to the reaction mixture caused a precipitate. The pH was made acidic with concentrated hydrochloric acid, whereupon the precipitate was filtered off and washed with several volumes of cold water over a glass filter. The product obtained was dried in vacuo.

Yield: 4.5 g.

EXAMPLE 17

DNPNH-CH$_2$CH(OMe)$_2$ and DNPNHCH$_2$CHO 2.03 g chloro-2,4-dinitrobenzene (10 mM) was added portionwise to a cold (0° C.), stirred solution of 5.26 g aminoacetaldehyde dimethyl acetal (5.45 ml; 50M) in 50 ml methanol. The stirring continued for 4 hours at 0° C. and 20 additional hours at room temperature. Then the solution was made acidic with 0.5N HCl solution, and more cold water was added.

Workup

The precipitate formed was filtered off and washed repeatedly with cold water, until the washings had a neutral pH. The produce was then dried in vacuo. Yield: 2.4 g.

regarded as a "DNP dimer" and thus as 2 euqivalents of DNP-NH(CH$_2$)$_2$NH$_2$ by the DCC coupling method. 1-Hydroxybenzotriazole (BTOH) was used as a catalyst and DMF as a solvent. A typical synthesis of this type was carried out as follows:

5 mM of the FMOC-L-amino acid was dissolved together with 5 mM 1-hydroxybenzotriazole in 15–50 g of dry DMF, whereupon the solution was cooled to between −10° to 15° C. DCC was added in excess, for most reactions 7.5 to 9.0 mM (50–80% excess). Cooling remained in effect for about 1 hour, and then the mixtures were allowed to react overnight. The workup was usually done by first adding 1–2 ml 1N HCl solution to the reaction mixture for destroying excess of DCC, except for FMOC-L-amino acids protected by acid sensitive groups, such as S-acetamidomethyl-L-cystein, TRT-L-histidine, MTR-L-Arginine, TRT-L-cysteine, PMC-L-Arginine, S-t-butyl-L-cysteine. Then the DCU formed was filtered off over a glass filter and it was washed with DMF until all yellow products had been washed out. The filtrate was made alkaline with a 5% NaHCO$_3$ solution and ice water added. The precipitate was washed repeatedly with cold water (usually over a Buchner filter) and dried in vacuo. In most cases the products obtained were already clean, but further purification could be achieved by recrystallisation from various solvents of mixtures thereof. The yields of the compounds ranged from 36–93%. The synthetic data of 20 different FMOC-L-amino acid DNP derivatives are compiled in Table 3.

TABLE 3

| Compound | Yield (%) | RF value in Ethylacetate: Ethanol = 0:1 | mp (0° C.) | Recrystallization mixture |
|---|---|---|---|---|
| 1 FMOC—L-Valine-DNP | 48 | 0.64 | 214.5–216 | — |
| 2 FMOC—L-Phenylalanine-DNP | 81 | 0.62 | 151–154 | CH$_3$OH:DMF = 9:4 |
| 3 FMOC—L-Leucine-DNP | 36 | 0.63 | 172–174 | CH$_3$OH:DMF = 8:1 |
| 4 FMOC—L-Glycine-DNP | 70 | 0.44 | 148–151 | CH$_3$OH:CH$_3$COOH |
| 5 FMOC—L-Isoleucine-DNP | 40 | 0.62 | 212–213.5 | CH$_3$OH:DMF = 1:1 |
| 6 FMOC-ε-BOC-L-Lysine-DNP | 80 | 0.57 | 169–171 | CH$_3$OH:DMF = 4:1 |
| 7 FMOC—L-Asparaginyl-DNP | 91 | 0.50 | 191–193 | CH$_3$OH:DMF = 2:1 |
| 8 FMOC—L-Methionine-DNP | 82 | 0.60 | 194–197 | CH$_3$:DMF |
| 9 FMOC—L-Aspartic acid | 71 | 0.64 | 133–136 | CH$_3$OH:DMF = 5:3 |
| 10 FMOC—L-Proline-DNP | 78 | 0.37 | 142–144 | CH$_3$OH:DMF = 2:1 |
| 11 FMOC—L-Tryptophan-DNP | 93 | 0.61 | 178.5–180.5 | CH$_3$OH:DMF = ? |
| 12 FMOC—L-Glutamic acid- -5-t-butylester-DNP | 77 | 0.63 | 187.5–189.5 | CH$_3$OH:DMF = 12:1 |
| 13 FMOC—O-t-butyl-L-Serine-DNP | 81 | 0.63 | 151–153 | CH$_3$OH:DMF = 19:1 |
| 14 FMOC—O-t-butyl-L-Tyrosine-DNP | 71 | 0.64 | 182–184 | CH$_3$OH:DMF = 3:1 |
| 15 FMOC—S-Acetamidomethyl- -L-Cysteine | 60 | 0.68 | 180–183 | CH$_3$OH:DMF = 3:1 |
| 16 FMOC-trityl-im-L-Histidine-DNP | 84 | 0.40 | 99–105 | CH$_3$OH:DMF:H$_2$O = 3:2:3 |
| 17 FMOC-Mtr-L-Arginine-DNP | 70 | 0.68 | 122–126 | CH$_3$OH:DMF = 7:1 |
| 18 FMOC-trityl-S-L-Cysteine-DNP | 81 | 0.47 | 119–122 | Hexane: etDAC = 2:1 |
| 19 FMOC-Pmc-L-Arginine-DNP | 42 | 0.47 | | CH$_3$OH:DMF = 3:1 |
| 20 FMOC—S-t-butyl-L-Cysteine- -DNP | 85 | 0.68 | 165–167 | EtOAc:EtOH(95%) = 4:1 |

EXAMPLE 18

FMOC-L-Amino Acid-DNP Derivatives

General Procedure:

The FMOC-L-amino acid DNP derivatives were all prepared from the N-protected FMOC-L-amino acids and DNPNH(CH$_2$)$_2$NH$_2$ or DNPNH(CH$_2$)$_2$NHCOONH(CH$_2$)$_2$NHDNP, which can be

EXAMPLE 19

Dansyl-SO$_2$NH(CH$_2$)$_2$NH$_2$

A solution of 134.3 mg dansyl chloride (0.5 mM) in 3 ml dry CH$_2$Cl$_2$ was slowly dropped (with a Pasteur pivette) into a cooled (0° C.) 0.6 g ethylene diamine (0.67 ml, 10 mM) in 5 ml dry Ca$_2$Cl$_2$. During the addition and therefafter, the solution of dansyl chloride and the reaction mixture was shielded from light. The reaction mixture was stirred for 45 minutes at 0° C., and another 15 minutes after cooling was taken away.

Workup

The reaction mixture was evaporated to dryness in vacuo, then taken up in 50 ml $CH_2Cl_2$. The solution was washed four times with 0.6N Kose. The organic layer was dried over $MgSO_4$. This was filtered off and the solvent was removed. Yield: 40 mg (27%), yellow oil.

EXAMPLE 20

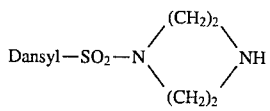

A solution of 135 mg dansyl chloride (0.5 mM) in 3 ml dry $CH_2Cl_2$ was dropped slowly into an ice cooled solution of 0.61 g piperazine (10 mM) in 15 ml dry $CH_2Cl_2$. The dansyl chloride solution was shielded from light during the addition and ensuing reaction. The reaction mixture was stirred for 2 hours at 0° C., and overnight at room temperature.

Workup

The reaction mixture was diluted with $CH_2Cl_2$ to about 60 ml, washed with 0.6N KOH (4×10 ml), dried over $MgSO_4$, filtered, and evaporated to dryness. Yield: 150 mg (94%), yellowish, fluorescent oil which crystallized upon standing.

EXAMPLE 21

It is possible, by using the reagents of this invention, to learn about the reaction path and side reactions of given reactions. For example, thyroxin peptides were reacted with t-butyloxycarbonyl anhydride ((t-BOC)$_2$O); part of the thyroxin was blocked with the t-BOC group to form the t-BOC-O phenyl derivative. When subjected to TLC on DNP NH(CH$_2$)$_2$NH$_2$ impregnated plates, the product and t-BOC DNPNH derivative was detected. By adding ammonia the t-BOC group was removed completely from the thyroxin and the pure thyroxin recovered.

This TLC with reagent impregnated along the base line can be used for (a) qualitative or quantitative detection or determination of functional groups, and (b) determining the reactivity of certain functional groups.

EXAMPLE 22

The Use of DNPNH(CH$_2$)$_3$OH in Sugar Transformations

1-Halo activated glucose tetra acetate, when reacted with DNPNH(CH$_2$)$_3$OH, yielded β- and α-glycosidic products in ratios of 96.4% β to 3.6% α, based on UV determination at 248 nm. When β and α products were separated and analyzed, their max and $E_M$ were identical, as expected.

The β-glucoside tetra acetate of glucose was hydrolyzed with a variety of hydroxylated or alkoxylated reagents, such as OH$^-$, O$^-$Me, O$^-$prop. In all cases hydrolysis takes place, but surprisingly enough, the amounts of tri- and di-acetate derivatives were found in small quantities, but monoacetate was already observed, even at the beginning of the reaction.

The use of the reagents of the present invention enabled the prediction of the existence of self-catalytic reactions in the sugar acetate molecule itself.

EXAMPLE 23

Triglyceride Analysis

Upon refluxing a fraction of 1 mg of a tri-glyceride with DNPNH(CH$_2$)$_3$NHNH$_2$ in toluene, cleavage of the glyceride esters occurred and the corresponding hydrazides were formed and analyzed quantitatively using H.P.L.C. separation.

EXAMPLE 24

The Use of Chiral Amines in the Determination of Chiral Amino Acids

When excess of HCl salt of -L-Val CONH(CH$_2$)$_2$NHDNP HCl was coupled to CbzDL-PheCO$_2$H using conventional peptide chemistry (DCC+OH Suc), the two diastereomers L—L and D—L of Cbz-Phe-Val-CO-NH(CH)$_2$DNP were separated by H.P.L.C., and their quantities were 1:1.

It will be evident to those skilled in the art that the invention is not limited to the details of the foregoing illustrative examples and that the present invention may be embodied in other specific forms without departing from the essential attributes thereof, and it is therefore desired that the present embodiments and example be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for the quantitative determination of an organic compound designated herein by A, said compound A having quantitatively reactable functional groups, said method consisting essentially of:

quantitatively reacting compound A, in a sample containing compound A, with a reagent comprising a compound of the general formula I:

$$Q\text{-}B\text{-}f \qquad (I)$$

wherein:

Q stands for an organic moiety which can be measured quantitatively, visually by color, spectroscopically, or fluorometrically;

B represents a non-reactive organic bridging unit linking the moiety Q to a reactive functional group f, said bridging unit including non-reactive $CH_2$—$CH_2$ linkages and being of sufficient length or size to prevent any possible interaction of Q that might alter its spectroscopic properties even upon derivatization; and f is a reactive group which can react with a compound to form covalently bonded derivatives, according to the reaction:

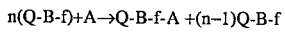

wherein: Q, B and f are as defined as above and n equals 1 or more;

separating any excess reagent (n−1)Q-B-f; and measuring the absorption of the reaction product Q-B-f-A wherein the molar absorptivity ε of said reaction product Q-B-f-A and said reagent Q-B-f are substantially constant and wherein the molar concentration of the reaction product Q-B-f-A is equal to the measured absorption divided by ε, whereby division of said measured absorption by ε provides the value of the molar concentration of the reaction product, thus eliminating the requirement for comparing the result with an external standard.

2. A method for the quantitative determination of an organic compound as claimed in claim 1, wherein said molar absorption is measured spectroscopically.

3. A method for the quantitative determination of an organic compound as claimed in claim 1, wherein said molar absorption is measured visually.

4. A method as claimed in claim 1, wherein A is an amino acid.

5. The method as claimed in claim 4 for determining mixtures of amino acids, comprising:

reacting said mixture of amino acids with said reagent of general formula I, separating the amino acid reaction products; and measuring said products spectroscopically with said reagent serving as a universal standard for all the amino acid reaction products.

6. A method for studying the reaction rates of a given functional group present in different types of compounds, comprising:

reacting a known mixture of compounds having the same functional group with less than stoichiometric amounts of a reagent comprising a compound of the general formula I:

$$Q\text{-}B\text{-}f \quad (I)$$

wherein:

Q stands for an organic moiety which can be measured quantitatively, visually by color, spectroscopically, or fluorometrically;

B represents a non-reactive organic bridging unit linking the moiety Q to a reactive functional group f, said bridging unit including non-reactive $CH_2$—$CH_2$ linkages and being of sufficient length or size to prevent any possible interaction of Q that might alter its spectroscopic properties even upon derivatization; and f is a reactive group which can react with a compound to form covalently bonded derivatives;

separating the derivative reaction products; and measuring the absorption of each derivative product using the reagent as a universal standard, wherein the molar absorptivity $\epsilon$ of each said derivative product is substantially the same, whereby division of said measured absorption of each said derivative product by the same value $\epsilon$ provides the value of the molar concentration of the derivative product and the reaction rates of the functional groups present in each of the different compounds are proportional to the molar concentration of each of the derivative products.

7. A method for studying reaction rates of functional groups as claimed in claim 6, wherein said reaction products are chromatographically separated.

8. A method for studying reaction rates of functional groups as claimed in claim 6, wherein said molar concentration is measured spectroscopically.

9. A method for studying the reaction rates of a given functional group present in different types of compounds, comprising:

reacting a known mixture of compounds having the same functional group with less than stoichiometric amounts of a reagent comprising a compound of the general formula I:

$$Q\text{-}B\text{-}f \quad (I)$$

wherein:

Q stands for an organic moiety which can be measured fluorometrically;

B represents a non-reactive organic bridging unit linking the moiety Q to a reactive functional group f, said bridging unit including non-reactive $CH_2$—$CH_2$ linkages and being of sufficient length or size to prevent any possible interaction of Q that might alter its fluorometrical properties even upon derivatization; and f is a reactive group which can react with a compound to form covalently bonded derivatives;

separating the derivative reaction products; and measuring the fluorescence of each derivative product using the reagent as a universal standard, wherein the molar absorptivity $\epsilon$ of each said derivative product is substantially the same, whereby division of said measured fluorescence of each said derivative product by the same value $\epsilon$ provides the value of the molar concentration of the derivative product and the reaction rates of the functional groups present in each of the different compounds are proportional to the molar concentration of each of the derivative products.

* * * * *